United States Patent
Amidi

(12) 
(10) Patent No.: US 10,864,347 B1
(45) Date of Patent: Dec. 15, 2020

(54) CHANGING SPOKEN LANGUAGE ACCENT BY PRESENTING A TRAINING AUDIO SEGMENT OF A TARGET ACCENT WHILE PRESENTING A RELAXING AUDIO SEGMENT

(71) Applicant: Erfan Amidi, Los Angeles, CA (US)

(72) Inventor: Erfan Amidi, Los Angeles, CA (US)

(*) Notice: Subject to any disclaimer, the term of this patent is extended or adjusted under 35 U.S.C. 154(b) by 300 days.

(21) Appl. No.: 16/014,237

(22) Filed: Jun. 21, 2018

Related U.S. Application Data

(63) Continuation of application No. 15/919,013, filed on Mar. 12, 2018, now abandoned.
(Continued)

(51) Int. Cl.
*A61M 21/00* (2006.01)
*A61M 21/02* (2006.01)
(Continued)

(52) U.S. Cl.
CPC .............. *A61M 21/02* (2013.01); *G09B 5/04* (2013.01); *G09B 19/04* (2013.01); *A61M 2021/0027* (2013.01)

(58) Field of Classification Search
CPC ... A61B 5/0482; A61B 5/0476; A61B 5/7267; A61B 5/7405; G16H 20/70; G09B 5/00;
(Continued)

(56) References Cited

U.S. PATENT DOCUMENTS

| 3,703,602 A | 11/1972 | Shenshev |
| 4,170,834 A | 10/1979 | Smart |

(Continued)

FOREIGN PATENT DOCUMENTS

| WO | 2004087246 A1 | 3/2004 |
| WO | 2016186590 A1 | 11/2016 |

OTHER PUBLICATIONS

"10 minute Guided Imagery" by City of Hope (https://www.youtube.com/watch?v=t1rRo6cgM_E (published Dec. 17, 2014, accessed Jun. 3, 2020; hereinafter City of Hope) (Year: 2014).*

(Continued)

*Primary Examiner* — Christine H Matthews
*Assistant Examiner* — Joshua Daryl D Lannu

(57) ABSTRACT

A method of changing or reducing accent, and/or improving accent by increasing the neuroplasticity of the brain using a repeating beat frequency pattern, while exposing the brain to proper pronunciation of words, phrases, sounds, and/or intonations during such increased neuroplasticity. The method includes presenting a relaxing audio segment that induces a relaxed receptive state in the language speaker, and then presenting a training audio segment that presents at least one model speaker pronouncing at least portions of speech in accordance with a target accent, while presenting the repeating beat frequency pattern. The relaxing audio segment can include instructions to promote relaxation in the listener's native language or in the target language. The method thereby enables learning pronunciations that are deeply rooted in the subconscious mind, so they sound natural and effortless when used. The method can be synergistically combined with more conventional methods of language learning to great benefit.

9 Claims, 3 Drawing Sheets

Related U.S. Application Data

(60) Provisional application No. 62/470,290, filed on Mar. 12, 2017.

(51) Int. Cl.
 *G09B 5/04* (2006.01)
 *G09B 19/04* (2006.01)

(58) Field of Classification Search
 CPC .......... G09B 19/00; G09B 5/06; G09B 5/065; G09B 7/00
 See application file for complete search history.

(56) References Cited

U.S. PATENT DOCUMENTS

| | | | |
|---|---|---|---|
| 5,224,864 A | 7/1993 | Vavagiakis | |
| 5,393,236 A | 2/1995 | Blackmer et al. | |
| 5,409,445 A | 4/1995 | Rubins | |
| 5,940,798 A | 8/1999 | Houde | |
| 5,995,932 A | 11/1999 | Houde | |
| 6,071,229 A | 6/2000 | Rubins | |
| 6,206,821 B1 | 3/2001 | Rhee | |
| 6,302,695 B1 * | 10/2001 | Rtischev | G09B 19/08 434/156 |
| 6,341,958 B1 | 1/2002 | Zilberman | |
| 7,299,188 B2 | 11/2007 | Gupta et al. | |
| 7,762,264 B1 | 7/2010 | Ramig et al. | |
| 8,050,541 B2 | 11/2011 | Gilbert et al. | |
| 8,175,882 B2 | 5/2012 | Basson et al. | |
| 8,672,681 B2 | 3/2014 | Markovitch | |
| 8,725,518 B2 | 5/2014 | Waserblat et al. | |
| 8,932,218 B1 * | 1/2015 | Thompson | A61B 5/7235 600/300 |
| 9,495,126 B2 | 11/2016 | Lang | |
| 2004/0006461 A1 * | 1/2004 | Gupta | G06F 40/58 704/200 |
| 2005/0282121 A1 * | 12/2005 | Zajur | G09B 19/06 434/157 |
| 2006/0247489 A1 | 11/2006 | Carbis et al. | |
| 2007/0009865 A1 | 1/2007 | Palacious | |
| 2007/0170306 A1 | 7/2007 | Weaver | |
| 2013/0143183 A1 | 6/2013 | Zilberman | |
| 2013/0302762 A1 | 11/2013 | Zhou et al. | |
| 2016/0314698 A1 | 10/2016 | Saada | |

OTHER PUBLICATIONS

Website: https://m.alibaba.com/guide/shop/focus-to-learn-german-faster-foreign-language-study-andself-help-with-hypnosis-meditation-relaxation-and-affirmations-the-sleep-learningsystem_58593328.html Downloaded Feb. 28, 2017 Focus to Learn German Faster: Foreign Language Study and Self Help with Hypnosis, Meditation, Relaxation, and Affirmations (The Sleep Learning System).

Website: http://www.testden.com/accent-reduction/ Downloaded Feb. 28, 2017 Accent Reduction Course The Accent Reduction Course is designed to help you eliminate your accent and sound just like a native English speaker.

Website: https://www.amazon.com/Reduce-Your-Accent-Subliminal-Affirmations/dp/B006VT08FQ Downloaded Feb. 28, 2017 Reduce Your Accent with Subliminal Affirmations: Speech Therapy & Pronucation Programi, Solfeggio Tones, Binaural Beats, Self Help Meditation Hypnosis Audible.

YouTube: https://www.youtube.com/watch?v=qX7yBY2xzLo Downloaded Mar. 4, 2017 Accent reduction hypnotherapy audio.

YouTube: https://www.youtube.com/watch?v=lNWCp5KTLQg Downloaded Mar. 4, 2017 Speak in a British Accent Subliminal.

Sheila Ostrander/Lynn Schroeder Superlearning Book published May 15, 1980 by Delta.

\* cited by examiner

CHANGING SPOKEN LANGUAGE ACCENT BY PRESENTING A TRAINING AUDIO SEGMENT OF A TARGET ACCENT WHILE PRESENTING A RELAXING AUDIO SEGMENT

CROSS-REFERENCES TO RELATED APPLICATIONS

This application is a Continuation Application of U.S. patent application Ser. No. 15/919,013 titled, "CHANGING SPOKEN LANGUAGE ACCENT BY PRESENTING A TRAINING AUDIO SEGMENT OF A TARGET ACCENT WHILE PRESENTING A RELAXING AUDIO SEGMENT" filed Mar. 12, 2018, which claims priority to U.S. Provisional Application Ser. No. 62/470,290, filed Mar. 12, 2017, titled "ACCENT CHANGE METHOD", both of which are herein incorporated by reference in their entirety.

FIELD OF THE INVENTION

This invention relates generally to auditory language learning, and more particularly to learning to better hear and more effectively produce sounds that make up a language so as to change or reduce one's accent speaking the language.

BACKGROUND OF THE INVENTION

Word pronunciations and spoken accents can be changed, and spoken accents can be reduced, when non-native speakers of a language learn to speak that language like a native speaker (e.g., a Chinese native would like to speak English with an American accent), or when a native speaker learns to speak with a different accent (e.g., when an American learns to speak English with a British accent, or with a reduced southern accent).

Known methods of accent reduction or accent change require that students learn different sounds, pronunciations, and rules of pronunciation in the language, and that the students practice the different pronunciations. For most students, especially older students, the known methods are either ineffective, or inadequate to make appreciable change.

After a certain age (between 7 and 9), the human brain starts to develop a logical mind, which filters and classifies sounds based on childhood experiences. For example, if there is no sound for voiced "Th" in the student's native language, such as in the word "That", the student's brain may classify that sound as "D", and so the student may pronounce the word "That" as "Dat". Due to lack of exposure to the voiced "Th" sound during childhood, in this example, the student's brain does not have a separate region for voiced "Th" and classifies voiced "Th" as "D".

Pronunciations that are learned during childhood are deeply rooted in the subconscious mind, so they sound natural and effortless when used. By contrast, conventional methods for accent change or improvement rely on pronunciations that are learned through conscious practice, so the pronunciations are not deeply rooted in the subconscious mind, therefore making the conventional accent change or accent reduction methods insufficient or entirely ineffective.

Another drawback to existing methods is that they rely on learning and practicing the rules of pronunciation. Real life conversations occur in a fast-paced manner, and the primary focus of the speaker should be on the contents of the conversation, not on the rules of proper pronunciation. Conscious attention on these rules makes the student's speech sound broken, awkward, and unnatural.

SUMMARY OF THE INVENTION

The present invention is a method for changing or reducing accent, and/or improving speech pronunciations by increasing the neuroplasticity of the brain (the brain's ability to change), while exposing the brain to the proper pronunciation of words, phrases, sounds, and intonations of a target accent during such increased neuroplasticity. Consequently, the brain can develop regions more sensitive to discrimination and perception of the sounds of the target accent.

A general aspect of the invention is method for changing accent in a spoken language of a listener. The method includes: presenting a relaxing audio segment configured to induce a relaxed receptive state in the listener; presenting a training audio segment after the relaxing audio segment, the training audio segment being configured to expose the listener to at least one model speaker pronouncing words and phrases in a target language in accordance with a target accent; and presenting a brainwave entrainment audio segment during at least the training audio segment, the brainwave entrainment audio segment being configured to induce alpha brainwave frequencies in the brain of the listener.

In some embodiments, the brainwave entrainment audio segment is presented during both the relaxing audio segment and the training audio segment.

In some embodiments, the brainwave entrainment audio segment includes a sequence of beat frequencies that vary in accordance with a predetermined pattern configured to enhance neuroplasticity.

In some embodiments, the brainwave entrainment audio segment includes a sequence of beat frequencies that vary in accordance with a repeating smoothed downward-sloping zig-zag pattern.

In some embodiments, the brainwave entrainment audio segment includes a sequence of beat frequencies that vary in accordance with a repeating smoothed downward-sloping zig-zag pattern, including: a maximum starting frequency value no more than 12.5 Hz; a first decreasing segment that decreases from the maximum starting frequency until reaching a first local minimum frequency; a first increasing segment that increases from the first local minimum frequency until it reaches a first local maximum frequency that is less than the maximum starting frequency; a second decreasing segment that decreases from the first local maximum frequency until reaching a second local minimum frequency; a second increasing segment that increases from the second local minimum frequency until it reaches a second local maximum frequency that is less than the first local maximum frequency; and a third decreasing segment that decreases from the second local maximum frequency until reaching a minimum ending frequency of no less than 7.5 Hz.

In some embodiments, the relaxing audio segment includes a guided imagery relaxation segment configured to guide the listener through imagery and suggestions to relax every part of his/her body.

In some embodiments, the relaxing audio segment includes instructions to promote relaxation. In further embodiments, the instruction to promote relaxation are in the listeners first language. In other further embodiments, the instructions to promote relaxation are in the language of the target accent.

In some embodiments, the relaxing audio segment includes instructions guiding the listener as to what to look at or what to visualize.

In some embodiments, the method further includes presenting instructions configured to aid the listener in learning the target accent.

In some embodiments, the instructions are in the language of the listener.

In some embodiments, the instructions are in the language of the target accent.

In some embodiments, the method further includes presenting instructions configured to aid the listener in using the target accent.

In some embodiments, the method further includes presenting instructions configured to aid the listener in learning the muscular movements of the target accent.

In some embodiments, the method further includes identifying component sounds of the target accent.

In some embodiments, the method further includes rehearsing component sounds needed to pronounce the target accent.

In some embodiments, the method further includes presenting instructions regarding best practices of pronunciation of the target accent.

In some embodiments, the method further includes repeating the method after changing the words and phrases, and/or word sounds of the training audio segment.

Another general aspect of the invention is a method for changing accent in a spoken language of a language speaker. This method includes: presenting a relaxing audio segment configured to induce a relaxed receptive state in the language speaker; and presenting a training audio segment configured to expose the listener to at least one model speaker pronouncing at least portions of speech in a target language in accordance with a target accent.

BRIEF DESCRIPTION OF THE DRAWINGS

Many additional features and advantages will become apparent to those skilled in the art upon reading the following description, when considered in conjunction with the accompanying drawings, wherein.

DETAILED DESCRIPTION

Figure 1:
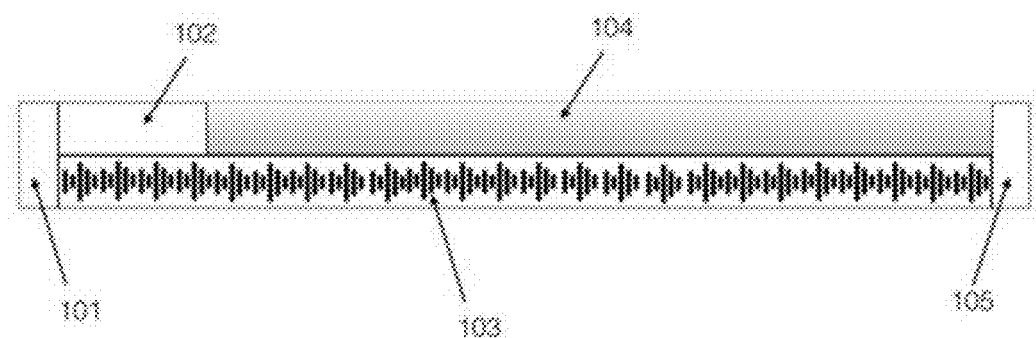
FIG. 1 is a time flow diagram showing a sequence of sequential and parallel auditory sequences of an embodiment of the method of the invention.

With reference to FIG. 1, a preparation segment 101 includes a brief orientation that invites the listener to eliminate distractions such as cell phones and alarms, adjust room temperature and ventilation, get comfortable in a chair or recliner, and do whatever else the person needs to do to remain focused for the duration of the session. The listener is advised to avoid coffee, tea, or other stimulants a few hours before the session.

The listener is also informed that the actual accent training segment 104 that will present spoken examples of the target accent is intended for the subconscious mind, so the listener should listen to the actual accent training segment 104 (explained further below) passively, rather than try to logically analyze the words and phrases presented. If the listener hears a word or phrase that is not immediately understood, it is suggested that the listener just let it go without trying to understand the word or phrase, and continue to listen passively. This preparatory information takes about a minute to present.

Then, guided breathing and relaxation instructions are presented for about two minutes. Preliminary, the listener is instructed to fix his/her eyes on a spot higher than eye level such as a spot on the wall or on the ceiling. Next, the listener is presented with timed breathing instructions. At this point, the pace of instructions slows down, and the listener is presented with suggestions that each breath makes him/her more relaxed. The timing between each inhalation and exhalation is 5 seconds. After about a minute of breathing in and out, the listener is presented with a suggestion to close his/her eyelids. In some embodiments (for less advanced speakers of the target language), the instructions in this section are in listener's first language. In other embodiments (for more advanced speakers of the target language), the instructions in this section are spoken in the target language, using the target accent.

A guided imagery relaxation segment 102 begins when the preparation segment 101 ends. Also, a brainwave entrainment audio segment 103 (explained further below) fades in when the preparation segment 101 ends. Thus, the brainwave entrainment audio segment 103 plays while the guided imagery relaxation segment 102 plays. Further, the brainwave entrainment audio segment 103 plays at an amplitude which is 10 times smaller than the amplitude of the guided imagery relaxation segment 102.

In the relaxation segment 102, the listener is guided through imagery and instructed to relax every part of his/her body. For example, the listener can be instructed to imagine that a ball of light enters his/her head from above, and as it goes through his/her head, face, arms, forearms, fingers, chest, torso, thighs, calves, and toes, every muscle in these body parts becomes completely relaxed. These body relaxation instructions in segment 102 last for about seven or eight minutes.

The listener can then instructed to imagine that they are in a safe and beautiful place with beautiful landscape for about one or two minutes. In some embodiments (for less advanced speakers of the target language), the instructions in this section are in listener's first language. In other embodiments (for more advanced speakers of the target language), the instructions in this section are spoken in the target language, using the target accent.

After the relaxation segment 102 ends, the training segment 104 fades in.

The brainwave entrainment audio segment 103 also continues to play while the training segment 104 plays. Further, the brainwave entrainment audio segment 103 plays at an amplitude which is 10 times smaller than the amplitude of the training segment 104.

Figure 2:
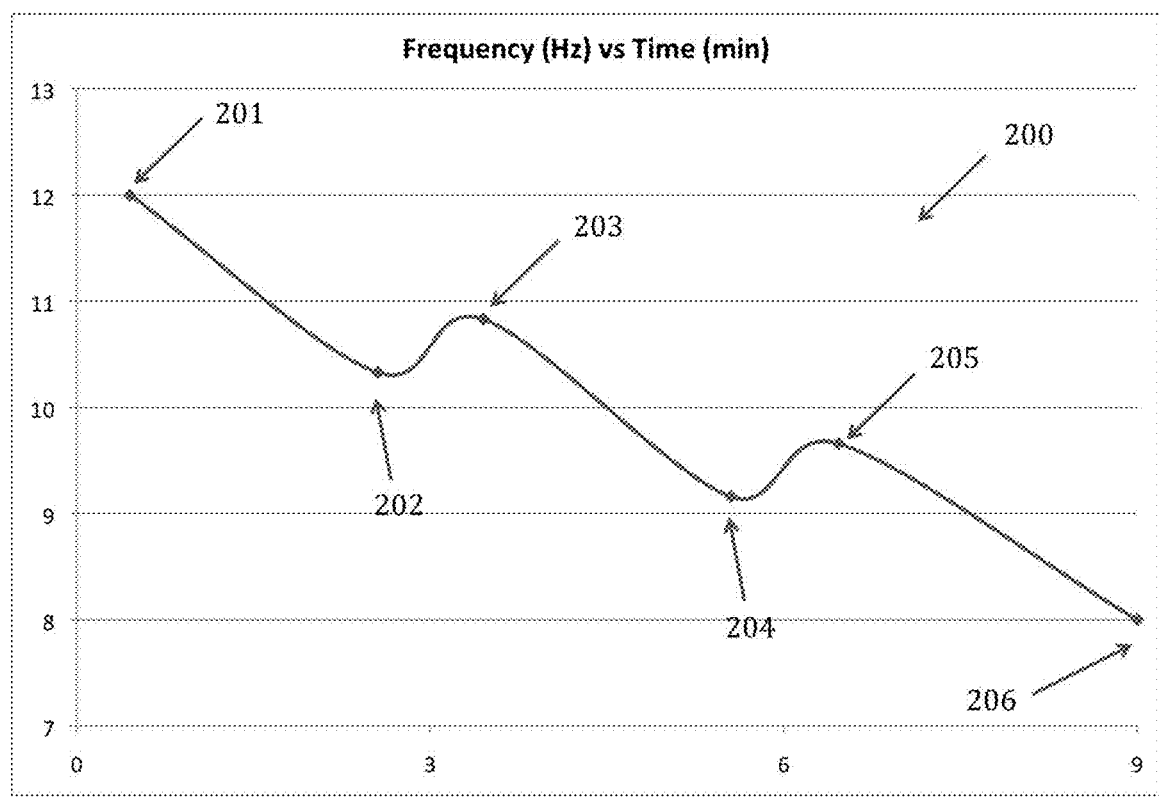
FIG. 2 is a plot of Frequency (Hz) vs Time (minutes) showing an exemplary shape of a repeating pattern of frequency change over time of a background sound configured to enhance neuroplasticity of regions of the brain that can learn new vocal sounds.

Referring to FIG. 2, the brainwave entrainment audio segment 103 will now be further explained. FIG. 2 shows a plot of Beat Frequency in Hz (cycles per second) vs Time in minutes.

To better induce relaxation, and to reduce resistance to unconscious learning of the sounds of the target accent, the beat frequency decreases in a downward-sloping zig-zag pattern from a maximum alpha value (e.g., 12 Hz) to a minimum alpha value of (e.g., 8 Hz) in 3-minute intervals, over three intervals, for a total of nine minutes.

Thus, in the graph in FIG. 2, the time ranges from 0 minutes to 9 minutes, and the frequency ranges from 12 Hz to 8 Hz. The frequency range of 12 Hz to 8 Hz falls within the range of "Alpha Waves". Alpha Waves are neural oscillations in the frequency range of 7.5 Hz to 12.5 Hz arising from synchronous and coherent (in phase or constructive) electrical activity of thalamic pacemaker cells in humans brains.

The pattern 200 of beat frequency variation over time shown in FIG. 2 is a smoothed downward-sloping zig-zag pattern including a maximum starting frequency value 201 of 12 Hz. The frequency then decreases until reaching a second frequency value 202 just before a local minimum, whereupon the frequency starts to increase until it reaches a local maximum just before a third frequency value 203. Thereafter, the frequency decreases as much as the decrease from the frequency at 201 to the frequency at 202, as the frequency decreases from the frequency at 203 to the frequency at 204. Then, a local minimum is reached, whereupon the frequency starts to increase as much as the increase from the frequency at 202 to the frequency at 203 until it reaches a local maximum just before a fifth frequency at 205. The frequency decreases thereafter as much as the decrease from the frequency at 203 to the frequency at 204, until the frequency at 206 is reached, i.e., 8 Hz. The changing beat frequency pattern is configured to present a sound stream that will tend to influence the listener's brain waves by "entrainment". Brainwave entrainment, also referred to as brainwave synchronization or neural entrainment, refers to the capacity of the brain to naturally synchronize its brainwave frequencies with the rhythm of periodic external stimuli, most commonly auditory, visual, or tactile. Brain wave "entrainment" in response to auditory beat frequencies is well-known in the art of altering brain wave frequencies using sound patterns, such as taught in Hewett, U.S. Pat. No. 7,647,224 B2.

The preferred pattern of beat frequencies shown in FIG. 2 takes 9 minutes to complete, and therefore the preferred pattern of beat frequencies will play almost once during the relaxation segment 102, and about 5 times during the training segment 104, and therefore about six times as the brainwave entrainment audio segment 103.

To create a non-changing 10 Hz beat frequency that is audible as an amplitude modulation, one can play a 245 Hz wave and along with a 255 Hz wave. The resulting combined wave has a frequency of 250 Hz modulated by a beat frequency envelope of 10 Hz. The 255 Hz frequency is heard, and its amplitude increases and decreases in accordance with a modulation "beat" frequency of 10 Hz. This can be computed using the Cosine "Sum-to-Product" rule for adding two waves:

$$\cos(2\pi 255 t) + \cos(2\pi 245 t) = 2 \cos(2\pi 250 t)\cos(2\pi 5 t)$$

The human brain responds to a 10 Hz beat frequency (which is double the 5 Hz from $\cos(2\pi 5t)$, because the ear can only detect the magnitude of the modulation) with brainwave frequency entrainment at 10 Hz. The predominant frequency of the firing of neurons in certain brain regions tends to match the beat frequency (e.g., 10 Hz) of the input sound wave.

To create a beat frequency that changes in accordance with the pattern as set forth in FIG. 2, the method of Hewett, U.S. Pat. No. 7,647,224 B2 can be used. Sound streams having changing beat frequencies for brainwave entrainment can be produced using beat frequency creation software, such as Neuro Programmer™, sold by Transparent Corp, Chicago, Ill. 60660, and explained in further detail at transparentcorp.com. Neuro Programmer™, creates alpha waves (8-12 Hz) by adding waves as explained above.

For an enhanced relaxation effect, gentle sounds (or white noise) can be added as a background sound to the sound that is amplitude-modulated by the changing beat frequency. In some embodiments, the gentle sounds include the sound of rain or the sound of a mountain stream or the sound of wind chimes or soothing tones.

In preferred embodiments, the sound modulated by changing beat frequencies is added to the background nature sounds using a mixing ratio of 10 to 1 in relative amplitude (not decibels). The final loudness (the volume) is controlled by the listener. However, the maximum decibel level on the audio is set at −6 db, which ensures that the listener is not startled and thereby forced to adjust the volume when the audio starts.

Brain waves in the frequency range of Alpha Waves are associated with relaxation and receptivity to learning, i.e., forming new neural connections in portions of the brain. In particular, the new neural connections correlate to learning new and more correct accents by forming new neural connections for hearing sounds of a target language that have not been effectively heard before, and forming new neural connections for producing sounds of a target language that have not been correctly pronounced with the target accent before. The relationship between learning and the alpha wave brain state has been described in Superlearning, Ostrander, et al, published by Delta (May 15, 1980).

Here is a partial list of scientific papers that assert that second-language learning and fluency can be achieved in adults, whereby new brain regions are created. For example: Hesling, I., Dilharreguy, B., Bordessoules, M. & Allard, M. (2012). The neural processing of second language comprehension modulated by the degree of proficiency: A listening connected speech fMRI study. Open Neuroimaging Journal, 6: 44-54.

This research shows through brain neuroimaging (PET) that native speakers and fluent speakers of the language as the second language use matching neural pathways in the brain, regardless of age. This rejects the "Crystallization Hypothesis" that second language speakers cannot develop similar neural pathway as native speakers. It also shows that the more fluent the second language speakers become, the more their brain resembles a native speaker's brain. In short, second language speakers can develop similar neural pathways and speak like natives.

Perani, D., Paulesu, E., Galles, N. S., Dupoux, E., Dehaene, S., Bettinardi, V., Cappa, S. F., Fazio, F. & Mehler, J. (1998). The bilingual brain: Proficiency and age of acquisition of the second language. Brain, 121, 1841-1852.

This study shows that the level of proficiency is a better determinant of similarity between native speakers and second language speakers, rather than age of acquisition of the second language.

Ventureyra, V. Pallier, C. & Yoo, Hi-Yon (2004). The loss of first language phonetic perception in adopted Koreans. Journal of Neurolinguistics, 17: 19-91.

This research rejects the idea of early imprinting of the language. In this study, fMRI is used to show that for immigrant children who were adopted and did not use their first language, the second language completely replaced their first language.

Kwok, V., Nui, Z., Kay, P., Zhou, K., Mo, L., Jin, Z., So, K.-F. & Tan, L. H. (2011). Learning new color names produces rapid increase in grey matter in the intact adult cortex. PNAS Early Edition: 1-3.

This study shows that the adult human brain is capable of new rapid growth when exposed to stimuli similar to what babies experience as they are learning from their environment.

Merzenich, M. M. & deCharms, R. C. (1996). Neural representations, experience, and change. In R. Llinas & P. S. Churchland (Eds.), The Mind-Brain Continuum: 61-81. Boston: MIT Press.

This study was done on monkeys to show that the brain becomes plastic, and can restructure, in a state of mindfulness, attention, and focus.

Leonard M. K., Torres, C., Travis, K. E., Brown. T. T., Hagler, D. J. Jr., Dale, A. M., Elman, J. L. & Halgren, E. (2011). Language Proficiency Modulates the Recruitment of Non-Classical Language Areas in Bilinguals. PLoS ONE, 6 (3): e18240. doi:10.1371/journal.pone.0018240 Is a Native-like Accent in a Foreign Language Achievable? Examining Neurological, Sociological, Psychological, and Attitudinal Factors This research shows that language proficiency is the determinant of similarity between brains when it comes to word processing, not whether the speaker is native or new.

According to the invention, adults learning a second-language, or adults that have used a second language fluently for years, but with an accent, can change their accent so as to resemble a native speaker of the language by using the method of the invention to train the brain to learn how to better discriminate the sounds of the target language, and to better pronounce the sounds of the target language, resulting in the creation of new brain regions dedicated to discriminating and hearing the new sounds of the target accent, and dedicated to correctly producing the new sounds of the target accent.

The core of the invention does not require conscious learning, since just passively listening to training samples of correct pronunciation while in an alpha state, induced by the simultaneous presentation of a stream of sound modulated by a beat frequency within the alpha frequency range, will result in the neural learning needed to change or improve or learn the target accent.

Nevertheless, one can synergistically combine the method of the invention with more conventional methods of conscious and/or analytical language learning to great advantage. That is because the method of the invention teaches the brain how to better discriminate and hear the sounds of the target language, and to better pronounce the sounds of that target language, thereby resulting in learning to more accurately produce the new sounds in accordance with the accent of native speakers of the target language. Thus, the method of the invention facilitates learning the fundamental sounds of a language, which can be synergistically combined with more conventional language learning that uses those fundamental sounds.

With reference to FIG. 1, the training segment 104 includes common conversations in various situations, as spoken by native speakers of the language, or by those fluent in the target accent. Words and phrases used in the conversations include the sounds of the language that are the cause of the accent for non-natives, and are more unique to the target accent. For example, in the case of American English, desired sounds include voiced and unvoiced "TH", Glottal "T", and Schwa.

In another embodiment, the conversations, words, and phrases are randomly presented, and are repetitive. Random and repetitive presentation of words, phrases, and constituent sounds of words and phrases are more readily absorbed by the subconscious mind when they are presented to the listener in a relaxed, receptive, and passive state, because they don't draw conscious attention to a specific storyline. These common conversations, words, sounds, and phrases are presented during the training segment 104 for 45 minutes.

Various embodiment of the training segment 104 include:
1) Common conversations based on various situations (e.g. conversations at college, conversations at work, conversation experienced as a visiting tourist)
2) Common conversations based on profession to help specific professionals (e.g. nurses, information technology support personnel, social workers)
3) Words and phrases with sounds that are specific to a target accent. For example, in the case of American English, voiced or unvoiced TH, Glottal T, or Schwa.
4) New sounds that are lacking in the native language/accent that are needed in the target accent, and important and common sounds in the target accent.
5) Words and phrases relating to: greetings and introductions, daily activities, planning and scheduling, expressing feeling and desires, making requests, offers, or asking for favors, expressing doubts or making decisions, future events, making a case or arguing, past events, verb tenses, and contractions.

Referring again to FIG. 1, after the training segment 104 and the brainwave entrainment audio segment 103 fade out, the ending segment 105 begins, including instructions that guide the listener to gradually open his/her eyes and end the session. During the ending segment 105, the pace of instructions become faster. The ending segment 105 has a duration of about a minute.

The Audio Session as explained with reference to FIG. 1 can be made and sold as a product or program presented to a listener. If the listener is new to the target language, all instructions are presented in the first language of the listener, except the conversations in the training segment 104. If the listener is more advanced in the target language, all instructions as well as the training segment 104 are in the target accent.

Figure 3:
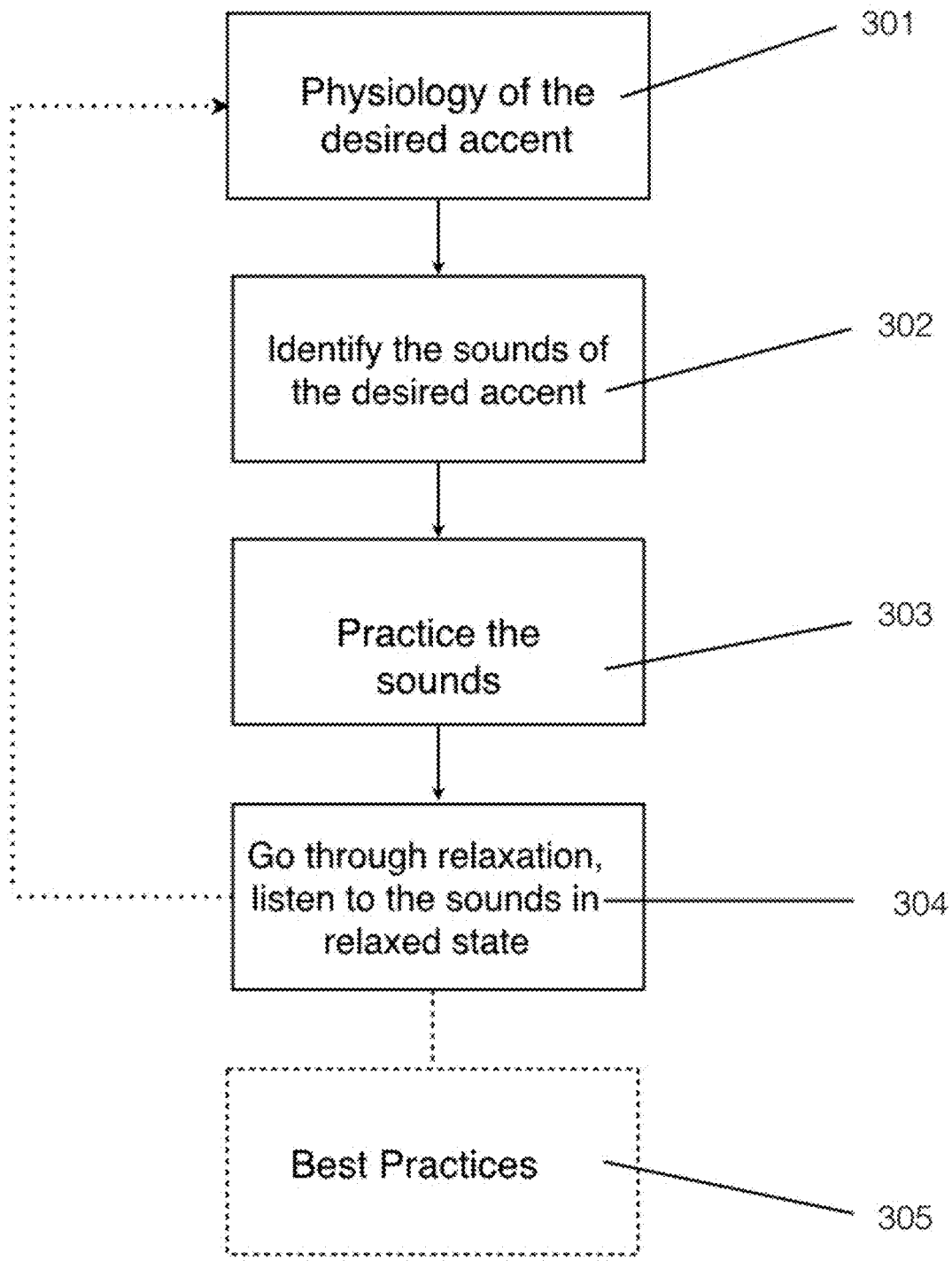
FIG. 3 is a flow diagram of steps of an embodiment of the method of the present invention.

With reference to FIG. 3, one embodiment of a product or program that incorporates the method of the invention has these additional components:

Segment 101 of FIG. 1 is preceded by instructions 301 regarding how to practice the physiology of the desired target accent. For example, for teaching a British accent, the student is instructed to practice speaking with the mouth more restrained and closed. For teaching an American accent, the student is instructed to practice speaking with mouth more wide open and relaxed.

Then, the sounds of the desired target accent are identified 302. The listener is presented with a list of languages to identify his/her first language from the list. Based on the listener's first language, a customized plan is created for the listener. The customized plan is created by comparing the listener's first language with the target accent to identify sounds and pronunciations that are vastly different or non-existent in the listener's first language compared to the target accent. The personal plan then recommends using training sessions 104 of FIG. 1 which emphasize those sounds for better results in accent change. If the listener's first language is not listed, a generic personal plan is created for the listener based on the most important sounds in the target accent.

Next, the listener is guided in active practice 303 of the sounds of the desired target accent.

Then, the listener can commence 304 with the method as set forth in FIG. 1, where the listener is guided in passive exposure to the sounds of the desired target accent.

The above steps 301-304 can be taken in an iterative and progressive manner, meaning that one sound can be chosen, and then the listener can proceed through all the steps for that specific sound until that sound is internalized, and then the listener can repeat the process for internalizing the next sound.

In some embodiments, the listener is presented with an ebook or physical book to instruct them in following rules that will improve the efficacy of the accent change program.

In some embodiments, segment 101 of FIG. 1 can be advantageously preceded by an orientation session that explains how the subconscious mind works and how these audio sessions are different from conventional classes.

In some embodiments, the segment 105 of FIG. 1 can be advantageously followed by presenting 305 a set of best practices that the listener should follow, such as:

do not use a dictionary to understand the meaning of a word or a phrase, do not study grammar; and do learn phrases, rather than learning individual words.

Other modifications and implementations will occur to those skilled in the art without departing from the spirit and the scope of the invention as claimed. Accordingly, the above description is not intended to limit the invention, except as indicated in the following claims.

What is claimed is:

1. A method for changing accent in a spoken language of a listener, the method comprising:
   presenting an audio segment configured to induce relaxation in the listener;
   presenting a training audio segment after the audio segment configured to induce relaxation, the training audio segment being configured to expose the listener to at least one model speaker pronouncing words and phrases in a target language in accordance with a target accent; and
   presenting a brainwave entrainment audio segment during at least the training audio segment, the brainwave entrainment audio segment being configured to induce alpha brainwave frequencies in the brain of the listener; and the brainwave entrainment audio segment includes a sequence of beat frequencies that vary in accordance with a repeating smoothed downward-sloping zig-zag pattern.

2. The method of claim 1, wherein the brainwave entrainment audio segment is presented during both the audio segment configured to induce relaxation and the training audio segment.

3. The method of claim 1, wherein the brainwave entrainment audio segment includes a sequence of beat frequencies that vary in accordance with a repeating smoothed downward-sloping zig-zag pattern, including:
   a maximum starting frequency value no more than 12.5 Hz;
   a first decreasing segment that decreases from the maximum starting frequency until reaching a first local minimum frequency;
   a first increasing segment that increases from the first local minimum frequency until it reaches a first local maximum frequency that is less than the maximum starting frequency;
   a second decreasing segment that decreases from the first local maximum frequency until reaching a second local minimum frequency;
   a second increasing segment that increases from the second local minimum frequency until it reaches a second local maximum frequency that is less than the first local maximum frequency; and
   a third decreasing segment that decreases from the second local maximum frequency until reaching a minimum ending frequency of no less than 7.5 Hz.

4. The method of claim 1, wherein the audio segment configured to induce relaxation includes:
   a guided imagery relaxation segment configured to guide the listener through imagery and suggestions to relax every part of a body of the listener.

5. The method of claim 1, wherein the audio segment configured to induce relaxation includes instructions to induce relaxation.

6. The method of claim 5, wherein the instructions to induce relaxation are not in the target language of the target accent.

7. The method of claim 5 wherein the instructions to induce relaxation are in the target language of the target accent.

8. The method of claim 1, further including:
   identifying component sounds of the target accent.

9. The method of claim 1, further including:
   rehearsing component sounds needed to pronounce the target accent.

* * * * *